US010823692B2

(12) United States Patent
Christenson et al.

(10) Patent No.: US 10,823,692 B2
(45) Date of Patent: Nov. 3, 2020

(54) MEMS DIE WITH SENSING STRUCTURES

(71) Applicant: Carrier Corporation, Palm Beach Gardens, FL (US)

(72) Inventors: John Carl Christenson, Prior Lake, MN (US); David P. Potasek, Lakeville, MN (US); Marcus Allen Childress, Farmington, MN (US)

(73) Assignee: CARRIER CORPORATION, Palm Beach Gardens, FL (US)

( * ) Notice: Subject to any disclaimer, the term of this patent is extended or adjusted under 35 U.S.C. 154(b) by 210 days.

(21) Appl. No.: 15/286,407

(22) Filed: Oct. 5, 2016

(65) Prior Publication Data

US 2017/0097314 A1 Apr. 6, 2017

Related U.S. Application Data

(60) Provisional application No. 62/237,955, filed on Oct. 6, 2015.

(51) Int. Cl.
*G01N 27/14* (2006.01)
*G01N 33/00* (2006.01)
(Continued)

(52) U.S. Cl.
CPC .............. *G01N 27/14* (2013.01); *B81B 7/02* (2013.01); *G01N 27/128* (2013.01);
(Continued)

(58) Field of Classification Search
CPC .. G01N 27/14; G01N 27/128; G01N 33/0027; G01N 33/0004; G01N 33/0036;
(Continued)

(56) References Cited

U.S. PATENT DOCUMENTS 4,928,513 A * 5/1990 Sugihara ................ G01N 27/12
338/34
5,019,885 A * 5/1991 Yagawara ............ G01N 27/123
257/414
(Continued)

FOREIGN PATENT DOCUMENTS

CN 102269724 A 12/2011
CN 102636544 A 8/2012
(Continued)

OTHER PUBLICATIONS

European Offce Action for application EP 16190207.7, dated Jan. 1, 2019, 7 pages.
(Continued)

*Primary Examiner* — Eric S. McCall
*Assistant Examiner* — Timothy P Graves
(74) *Attorney, Agent, or Firm* — Cantor Colburn LLP

(57) ABSTRACT

A microelectromechanical systems die including a thermally conductive substrate including an outer surface, a plurality of low mass sensing structures disposed within the thermally conductive substrate to form a plurality of inter-structure spaces therebetween, each of the plurality of low mass sensing structures include a sensing structure proximal top surface, a sensing structure distal top surface, and a sensing structure width dimension.

23 Claims, 7 Drawing Sheets

(51) Int. Cl.
  *G01N 27/12* (2006.01)
  *B81B 7/02* (2006.01)

(52) U.S. Cl.
  CPC ..... *G01N 33/0004* (2013.01); *G01N 33/0027* (2013.01); *G01N 33/0036* (2013.01); *B81B 2201/00* (2013.01); *B81B 2201/02* (2013.01); *B81B 2201/0214* (2013.01)

(58) Field of Classification Search
  CPC ... B81B 7/02; B81B 2201/02; B81B 2201/00; B81B 2201/0214
  See application file for complete search history.

(56) References Cited

U.S. PATENT DOCUMENTS

| | | | |
|---|---|---|---|
| 6,180,536 | B1 | 1/2001 | Chong et al. |
| 6,239,473 | B1 | 5/2001 | Adams et al. |
| 6,329,679 | B1 | 12/2001 | Park |
| 6,342,430 | B1 | 1/2002 | Adams et al. |
| 6,533,554 | B1 * | 3/2003 | Vargo .............. F04B 19/006 |
| | | | 417/207 |
| 6,593,163 | B1 | 7/2003 | Bonin et al. |
| 7,060,197 | B2 | 6/2006 | Fuertsch et al. |
| 7,116,462 | B2 | 10/2006 | Ikeda |
| 7,354,786 | B2 | 4/2008 | Benzel et al. |
| 7,859,091 | B2 | 12/2010 | Fujii et al. |
| 7,943,525 | B2 | 5/2011 | Zhang et al. |
| 8,455,973 | B2 | 6/2013 | Fujii et al. |
| 8,679,975 | B2 | 3/2014 | Reinmuth et al. |
| 8,749,019 | B2 | 6/2014 | Fujii et al. |
| 2005/0023656 | A1 * | 2/2005 | Leedy .................. B81B 7/02 |
| | | | 257/678 |
| 2006/0160264 | A1 * | 7/2006 | McDonald .......... B81C 1/00309 |
| | | | 438/51 |
| 2006/0185980 | A1 | 8/2006 | Fukuda |
| 2007/0170057 | A1 * | 7/2007 | Kobayashi ......... G01N 27/4071 |
| | | | 204/424 |
| 2010/0147070 | A1 | 6/2010 | Jun et al. |
| 2010/0166614 | A1 | 7/2010 | Uchiyama et al. |
| 2012/0194669 | A1 * | 8/2012 | Hutto .................... G01N 21/05 |
| | | | 348/135 |
| 2014/0138259 | A1 | 5/2014 | Mickelson et al. |
| 2014/0260546 | A1 * | 9/2014 | Chen .................... G01N 27/128 |
| | | | 73/31.06 |

FOREIGN PATENT DOCUMENTS

| | | | |
|---|---|---|---|
| CN | 204008531 U | 12/2014 | |
| JP | 2011033592 A * | 2/2011 | ............. G01N 27/12 |

OTHER PUBLICATIONS

Frey, Urs et al., "A Digital CMOS Architecture for a Micro-Hotplate Array", IEEE Journal of Solid-State Circuits, vol. 42, No. 2, Feb. 2007, pp. 441-450.

Mo, Yaowu et al., "Micro-machined gas sensor array based on metal film micro-heater", Sensors and Actuators B 79, 2001, pp. 175-181.

Zee, Frank et al., "Micromachined polymer-based chemical gas sensor array", Sensors and Actuators B 72, 2001, pp. 120-128.

Muller, G. et al., "A MEMS toolkit for metal-oxide-based gas sensing systems", Thin Solid Films, vol. 436, No. 1, Jul. 22, 2003, pp. 34-45.

* cited by examiner

MEMS DIE WITH SENSING STRUCTURES

CROSS-REFERENCE TO RELATED APPLICATIONS

The present application is a nonprovisional patent application, which claims priority to 62/237,955, filed Oct. 6, 2015, which is herein incorporated in its entirety.

TECHNICAL FIELD OF THE DISCLOSED EMBODIMENTS

The present disclosure is generally related to the art of microelectromechanical (MEMS) devices, and more particularly, to MEMS dies with sensing structures.

BACKGROUND OF THE DISCLOSED EMBODIMENTS

Generally, gas detector devices are constructed on a substrate, often made of ceramic. A chemo-resistive material (i.e. sensing element) is disposed on the substrate and is largely thermally isolated from its surroundings. The gas detector may have a method of heating and sensing the temperature on the sensing element on the surface of the substrate that connects two conductive terminals. In operation at an appropriate temperature, and under normal circumstances, the sensing element generally has a high electrical resistance; however, when exposed to a specific gas, the sensing element experiences a drop in resistance of several orders of magnitude. This may be used to detect the presence of a gas in different applications.

Chemo-resistive gas sensing is generally a surface phenomenon. As such, most chemo-resistance gas detector devices feature a single, surface, planar chemo-resistant film disposed between two electrodes. As a result the size of the substrate and other design considerations limit the amount of surface area for the sensing element.

Accordingly, there exists a need for improvements in chemo-resistive gas detectors to increase the surface area of the sense element without increasing the size of the substrate and improve performance of a gas detector.

SUMMARY OF THE DISCLOSED EMBODIMENTS

In one aspect a microelectromechanical systems die is provided. The microelectromechanical systems die includes a thermally conductive substrate including an outer surface, and a plurality of low mass sensing structures disposed within the thermally conductive substrate to form a plurality of inter-structure spaces therebetween, each of the plurality of low mass sensing structures include a sensing structure proximal top surface, a sensing structure distal top surface, and a sensing structure width dimension.

In an embodiment of the die, at least two of the plurality of sensing structures include a different sensing structure width dimension. In any embodiment of the die, the thermally conductive substrate is composed of silicon.

In any embodiment, the die further includes a sensor material disposed on each of the plurality of low mass sensing structures. In one embodiment, the die further includes a first electrode disposed on the sensor material at the sensing structure proximal top surface, and a second electrode disposed on the sensor material at the sensing structure distal top surface.

In any embodiment, the die further includes a heating apparatus disposed on each of the plurality of low mass sensing structures. In any embodiment of the die, at least one dielectric film is disposed over the thermally conductive substrate. In one embodiment, at least one aperture is disposed within the at least one dielectric film.

In any embodiment, the die further includes a plurality of passive heat exchangers, each operably coupled to a bond pad, wherein each bond pad is disposed on each of the at least one low mass sensing structures. In one embodiment, the bond pad is operably coupled to at least one of the at least one electrode and the heating apparatus.

In any embodiment, the die further includes at least one channel disposed within the thermally conductive substrate, wherein the at least one channel extends from the outer surface into at least one of the plurality of inter-structure spaces. In an embodiment, a cavity is disposed within the thermally conductive substrate, the cavity disposed beneath each of the plurality of low mass sensing structures, and in flow communication with the at least one channel.

In one embodiment, the die further includes a sacrificial coating disposed on at least one of the plurality of low mass sensing structures, wherein the sacrificial coating is disposed over the sensor material. In one embodiment, the sacrificial coating is configured to be removed by the heating apparatus. In one embodiment, the sacrificial coating is composed of at least one of an organic material and a plastic material.

In one aspect, gas detector package is provided. The gas detector package includes a microelectromechanical systems die including a thermally conductive substrate, and a plurality of low mass sensing structures disposed within the thermally conductive substrate, the plurality of low mass sensing structures including a sensing structure proximal top surface, a sensing structure distal top surface, and a sensing structure width dimension. In any embodiment of the package, at least two of the plurality of sensing structures include a different sensing structure width dimension. In any embodiment of the package, the thermally conductive substrate is composed of silicon.

In any embodiment, the package further includes a sensor material disposed on each of the plurality of low mass sensing structures. In one embodiment, the package further includes a first electrode disposed on the sensor material at the sensing structure proximal top surface, and a second electrode disposed on the sensor material at the sensing structure distal top surface.

In any embodiment, the package further includes a heating apparatus disposed on each of the plurality of low mass sensing structures. In any embodiment of the package, at least one dielectric film is disposed over the thermally conductive substrate. In one embodiment, at least one aperture is disposed within the at least one dielectric film.

In any embodiment, the package further includes a plurality of passive heat exchangers, each operably coupled to a bond pad, wherein each bond pad is disposed on each of the at least one low mass sensing structures. In one embodiment, the bond pad is operably coupled to at least one of the at least one electrode and the heating apparatus.

In any embodiment, the package further includes at least one channel disposed within the thermally conductive substrate, wherein the at least one channel extends from the outer surface into at least one of the plurality of inter-structure spaces. In an embodiment, a cavity is disposed within the thermally conductive substrate, the cavity disposed beneath each of the plurality of low mass sensing structures, and in flow communication with the at least one channel.

In one embodiment, the package further includes a sacrificial coating disposed on at least one of the plurality of low mass sensing structures, wherein the sacrificial coating is disposed over the sensor material. In one embodiment, the sacrificial coating is configured to be removed by the heating apparatus. In one embodiment, the sacrificial coating is composed of at least one of an organic material and a plastic material.

DETAILED DESCRIPTION OF THE DISCLOSED EMBODIMENTS

Figure 1:
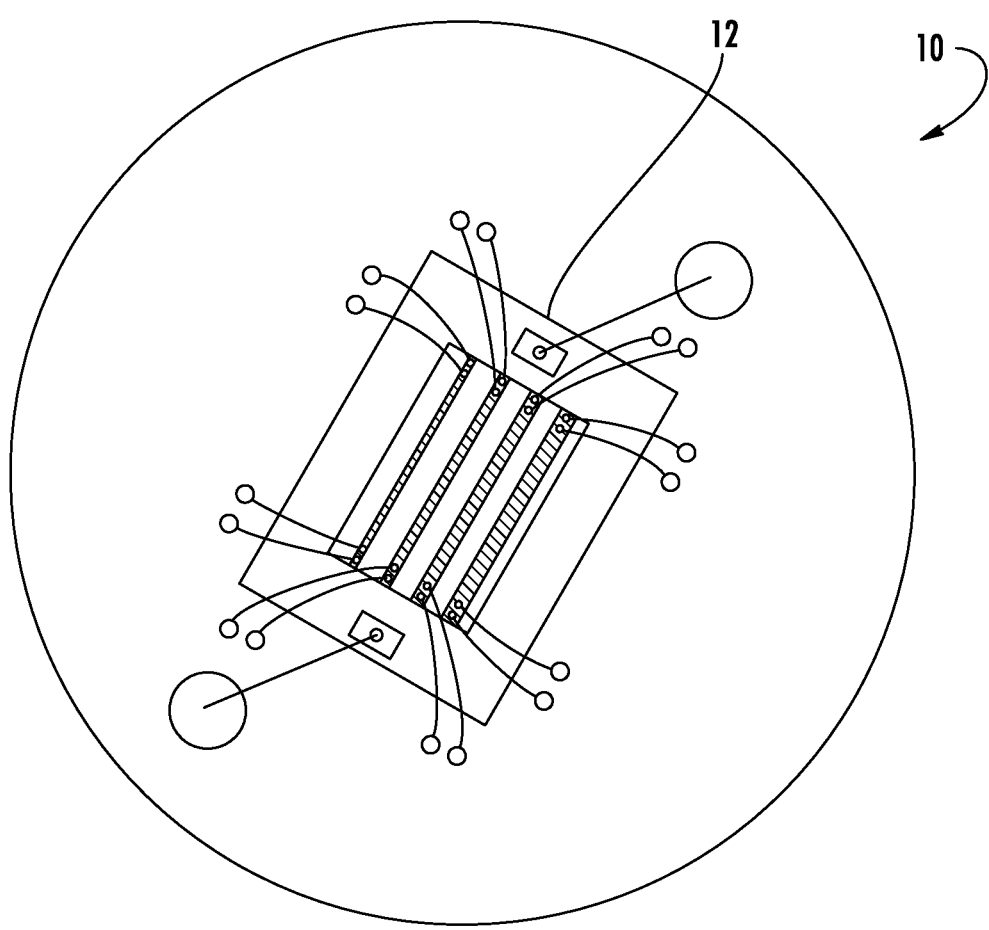
FIG. 1 illustrates a schematic drawing of gas detector sensor according to one embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

Figure 2:
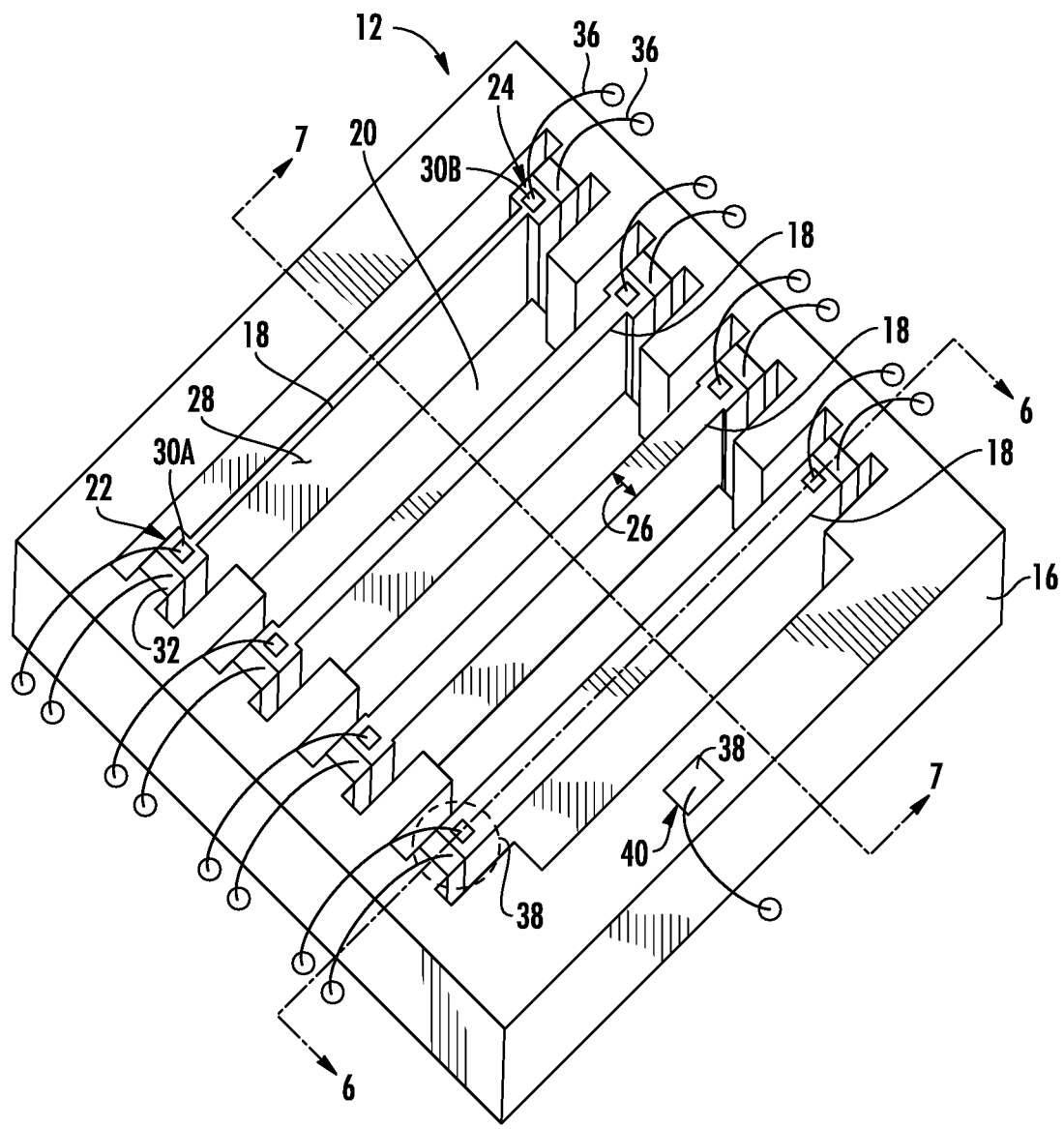
FIG. 2 illustrates a perspective view of a microelectromechanical systems die according to one embodiment of the present disclosure.

FIG. 1 illustrates an embodiment of a gas detector device, generally indicated at 10. The gas detector device 10 includes a microelectromechanical systems (MEMS) die 12. With reference to FIG. 2, the MEMS die 12 includes a thermally conductive substrate 16. In an embodiment, the thermally conductive substrate 16 is composed of silicon.

The MEMS die 12 further includes a plurality of low mass sensing structures 18 disposed within the thermally conductive substrate 16. The plurality of low mass sensing structures 18 are formed by creating a plurality of inter-structure spaces 20 within the thermally conductive substrate 16. Each of the plurality of low mass sensing structures 18 includes a sensing structure proximal top surface 22, a sensing structure distal top surface 24, and a low mass sensing structure width dimension 26. In an embodiment, at least two of the plurality of low mass sensing structures 18 includes a different sensing structure width dimension 26.

It will be appreciated that the low mass sensing structures 18 may have any length, width, size and shape, and cross section geometries, including straight or folded, and is anticipated in the present disclosure. It will be further appreciated that the low mass sensing structures 18 may be placed in any orientation within the thermally conductive substrate 16, including origins and insertions on any sidewall of the thermally conductive substrate 16.

An embodiment may have multiple connections of a low mass sensing structure 18 to the thermally conductive substrate 16. In some embodiments, the low mass sensing structures 18 may be interdigitated. In an embodiment, the low mass sensing structures 18 may be separated by equal, unequal, or varying dimension inter-structure spaces 20. In an embodiment the low mass sensing structures 18 may be separated by a combination of inter-structure spaces 20 and/or one or more spacers (not shown). It will be appreciated that the one or more spacers may be comprised of functional or non-functional low mass sensing structures 18.

The MEMS die 12 further includes sensor material 28 (see FIGS. 7-8) disposed on each of the plurality of low mass sensing structures 18. The sensor material 28 is configured to detect the presence of a target gas as it passes over the sensor material 28 and between the plurality of the low mass sensing structures 18 through the inter-structure spaces 20. It will be appreciated that the sensor material 28 may be disposed on any side or all sides of the low mass sensing structures 18.

The MEMS die 12 further includes at least one electrode 30 disposed on each of the plurality of the low mass sensing structures 18. In an embodiment, the at least one electrode 30 includes a first electrode 30A disposed on the sensor material 28 at the sensing structure proximal top surface 22, and a second electrode 30B disposed on the sensor material 28 at the sensing structure distal top surface 24. The at least one electrode 30 is configured to send an electrical signal across the sensing material 28 disposed on each of the low mass sensing structures 18. It will be appreciated that the at least one electrode 30 may be composed of gold, or aluminum to name a couple of non-limiting examples.

The MEMS die 12 further includes a heating apparatus 32 disposed on each of the plurality of low mass sensing structures 18. Each heating apparatus 32 is configured to operate as a hot plate which may independently control the temperature of the sensor material 28 on each of the plurality of low mass sensing structures 18 by applying a current through the heating apparatus 32 to enable the independent detection of different gasses at the same time. Each of the heating apparatus 32 may be utilized to maintain a constant temperature or to control a predetermined time varying temperature on each of the low mass sensing structures 18, independently of any other low mass sensing structure 18, in any environment. Additionally, each of the heating apparatus 32 may be used to monitor the temperature of the sensor material 28. In one embodiment, each heating apparatus 32 may be configured to hold a low mass sensing structure 18 at a constant temperature. In another embodiment, each heating apparatus 32 may also be configured to cause a low mass sensing structure 18 to cycle through an advantageous range of temperatures. In another embodiment, one heating apparatus 32 may be configured to hold at least one low mass sensing structure 18 at a fixed temperature, while another heating apparatus 32 may be configured to vary the temperature of a different low mass sensing structure 18.

In an embodiment, as shown in FIG. 2 the contact (i.e. bond pad 38) to the heating apparatus 32 is disposed between the connection of the low mass sensing structure 18 to the thermally conductive substrate 16 and the at least one electrode 30 at both the proximal and distal ends of the low mass sensing structure 28. In an embodiment the contact (i.e. bond pad 38) to the heating apparatus 32 is disposed between the at least one electrode 30 and the sensor material 28 at both the proximal and distal ends of the low mass sensing structure 18, effectively thermally isolating the low mass sensing structure 18 from all other structures of the MEMS device, including the thermally conductive substrate 16, the at least one electrode 30, and at least one passive heat exchangers 36 (as later described herein), which are operably coupled to bond pads 38. It will be appreciated that the heating apparatus 32 may be composed of platinum and nickel to name a couple of non-limiting examples, and contain a corrosion prevention coating. It will also be appreciated that the heating apparatus 32 may be disposed largely underneath the at least one electrode 30 and sensor material 28.

Figure 3:
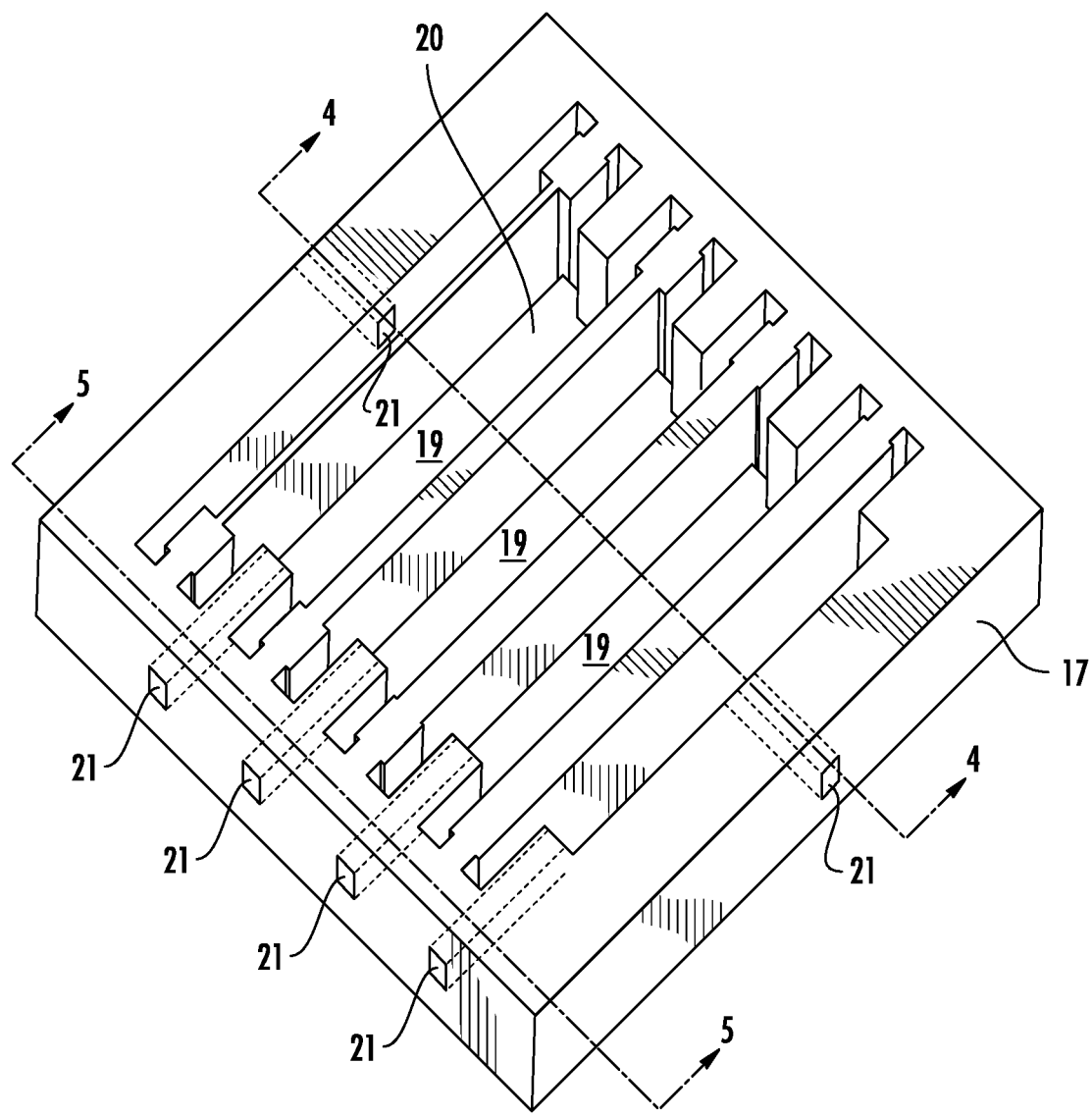
FIG. 3 illustrates a perspective drawing of gas detector sensor according to one embodiment of the present disclosure.
Figure 4:
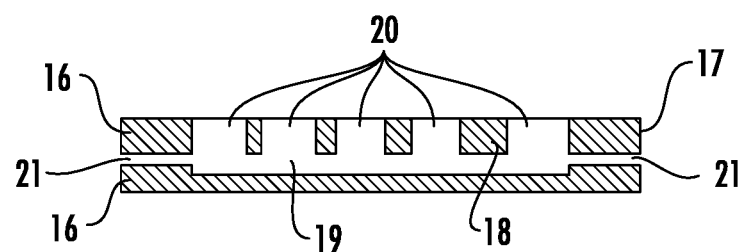
FIG. 4 illustrates a cross-sectional view of a microelectromechanical systems die according to one embodiment of the present disclosure.
Figure 5:
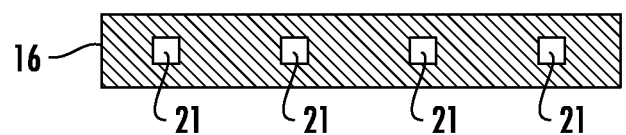
FIG. 5 illustrates a cross-sectional view of a microelectromechanical systems die according to one embodiment of the present disclosure.

In an embodiment, as shown in FIGS. 3-5, the MEMS die 12 further includes at least one channel 21 disposed within the thermally conductive substrate 16. The at least one channel 21 extends from an outer surface 17 of the thermally conductive substrate 16 into the inter-structure spaces 20. In another embodiment, as shown in FIG. 4, a cavity 19 is present within the thermally conductive substrate 16, and is located beneath each of the low mass sensing structures 18. The cavity 19 may be accessed via the at least one channel 21 formed within the thermally conductive substrate 16 through which gasses may pass.

Figure 6:
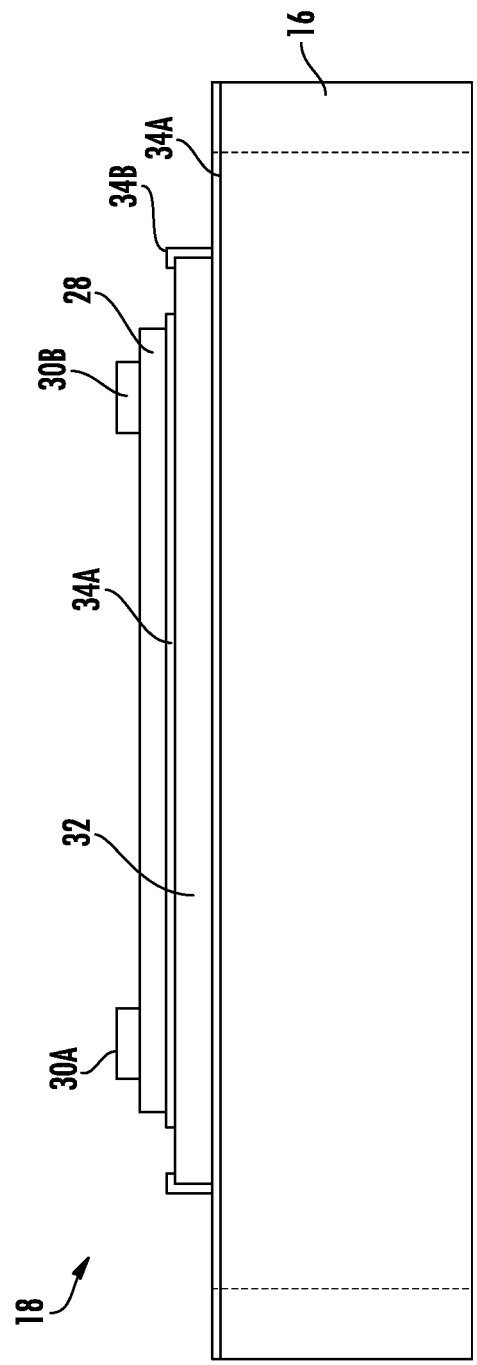
FIG. 6 illustrates a cross-sectional view of a microelectromechanical systems die according to one embodiment of the present disclosure.
Figure 7:
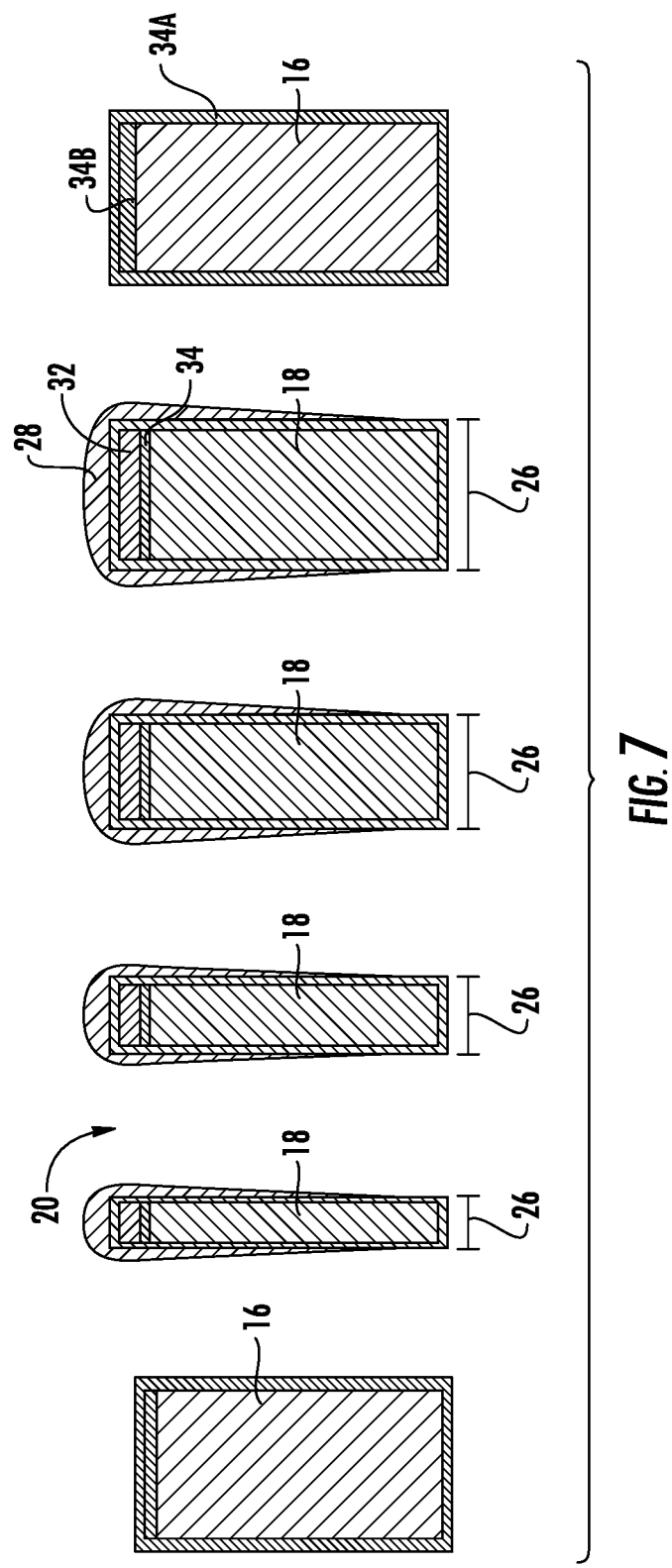
FIG. 7 illustrates a cross-sectional view of a microelectromechanical systems die according to one embodiment of the present disclosure.
Figure 8:
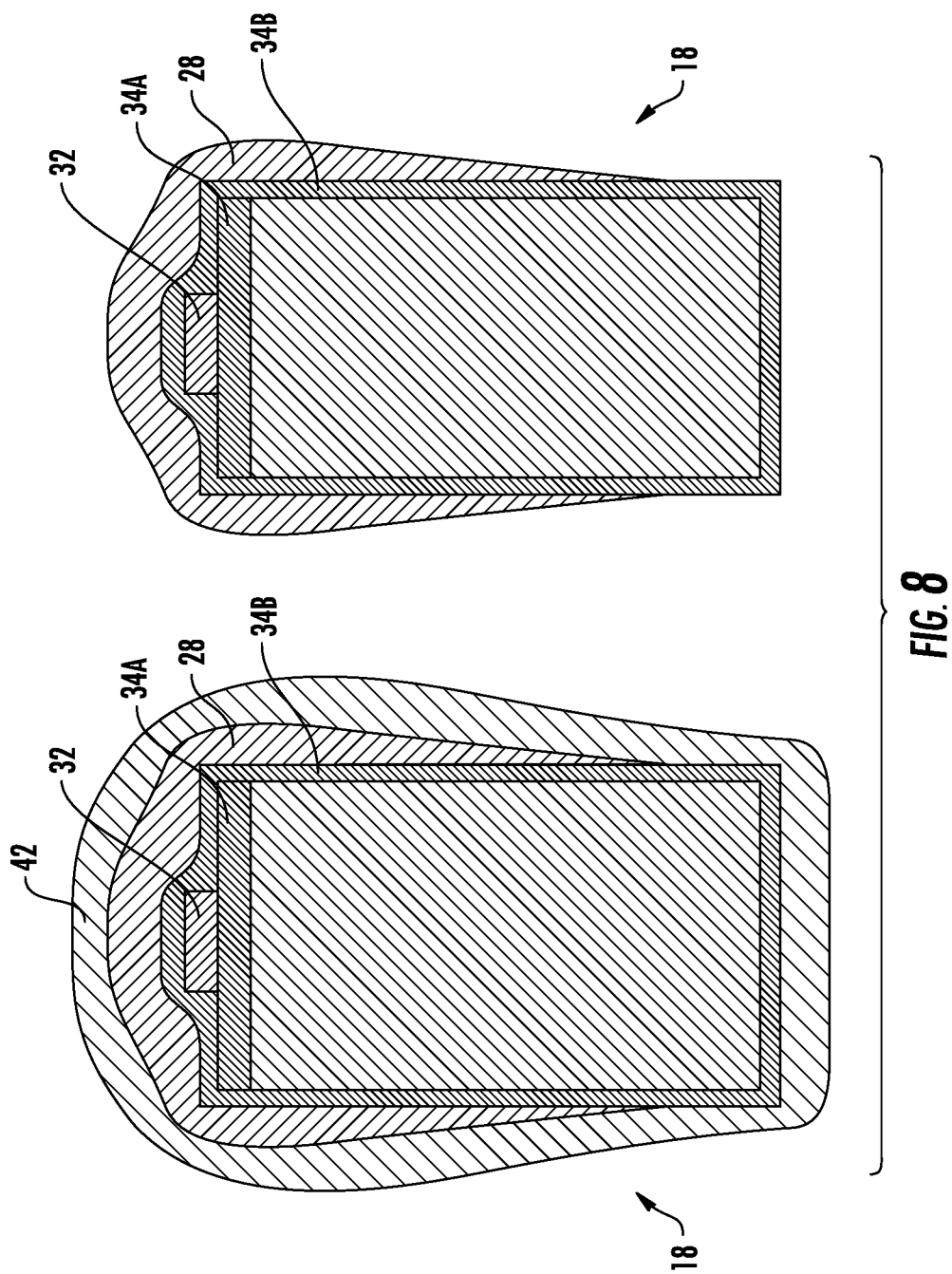
FIG. 8 illustrates a cross-sectional view of a sensing structure within a microelectromechanical systems die according to one embodiment of the present disclosure.

In an embodiment, the MEMS die 12 includes at least one dielectric film 34 (shown in FIGS. 6-8) disposed over the thermally conductive substrate 16. For example, the at least one dielectric film 34 may include two sets of two different dielectric films 34A, 34B, as shown in FIGS. 6-8. The two sets of two dielectric films 34A, 34B may be deposited in an order: A, B, A. In the embodiments shown in FIGS. 6-8, the two dielectric films 34A, 34B may be such that the A dielectric films are composed of silicon nitride and the B dielectric films are composed of silicon dioxide to name a couple of non-limiting examples.

It will be appreciated that the heating apparatus 32 may be disposed on or between any of the at least one dielectric film 34, or on a bottom surface of the thermally conductive substrate 16. It may be further appreciated that the heating apparatus 32 may be enclosed by combinations of the at least one dielectric film 34. Enclosing the heating apparatus 32 may prevent electromigration or corrosion of the heating apparatus 32 material. For example, enclosing the heating apparatus 32 with a silicon dioxide film may also prevent silicide formation.

It will also be appreciated that the at least one dielectric film 34 may be deposited prior to formation of the at least one electrode 30 and heating apparatus 32, and that a second set of dielectric film 34 may be deposited after the at least one electrode 30 and heating apparatus 32 have been formed, so as to enclose portions of each of the at least one electrode 30 and heating apparatus 32.

In another embodiment, MEMS die 12 further includes a plurality of passive heat exchangers 36, each operably coupled to a bond pad 38. Each bond pad 38 is disposed on each of the at least one sensing structure 18. In one embodiment, the bond pad 38 is operably coupled to the at least one electrode 30 and the heating apparatus 32. For example, each of the plurality of passive heat exchangers 36 may be a wire bond configured to provide a connection means of electrical input and output to at least the at least one electrode 28 and heating apparatus 30.

It will be appreciated that each of the plurality of passive heat exchangers 36 may be coupled to each bond pad 38 by any means known in the art, for example wire bonding, foil bonding, bump and flip chip to name a few non-limiting examples. It will also be appreciated that the each of the plurality of passive heat exchangers 36 is part of a thermal isolation scheme to exchange heat between the MEMS die 12 and a gas detector package/environment, and include small diameters and long lengths to reduce the rate at which heat is transferred.

In some embodiments, the plurality of passive heat exchangers 36 are coupled to place the MEMS die 12 in a spider die (i.e. floating die) configuration; however, it will be appreciated that the sensor material 28 on the MEMS die 12 may be substantially thermally isolated from its mounting by a number of configurations, such as a membrane isolating a central heated mass, tethers isolating a central heated mass, a diaphragm or perforated diaphragm isolating a central mass, a cantilevered mounting, etc. to name a few non-limiting examples. It will further be appreciated that the MEMS die 12 may be mounted to a plastic, ceramic, or TO packages to name a few non-limiting examples.

In an embodiment, the MEMS die 12 further includes at least one aperture 40 disposed within the at least one dielectric film 34. The at least one aperture 40 forms a contact point with the thermally conductive substrate 16, and is configured to provide an insulation resistance verification of the at least one dielectric film 34, and allows for testing and diagnostics of the MEMS die 12. In an embodiment, a passive heat exchanger 36 operably coupled to a bond pad 38 may be disposed within the aperture 40. For example, the passive heat exchangers 36 may be a wire bond configured to provide a connection means of electrical input and output to the aperture 34.

In an embodiment, as shown in FIG. 8, the MEMS die 12 further includes a sacrificial coating 42 disposed on at least one of the low mass sensing structures 18. In an embodiment, the sacrificial coating 42 is composed of at least one of an organic material and a plastic material. It will be appreciated that other materials may be used for the sacrificial coating 42. The sacrificial coating 42 is configured to reduce a chemical reaction with the low mass sensing structures 18 to increase the longevity of the MEMS dies 12 by only removing the sacrificial coating 42 when needed. In an embodiment, the sacrificial coating 42 may be removed by operating the heating apparatus 32 at a temperature to burn away the sacrificial coating 42.

It will therefore be appreciated that the present embodiments include a MEMS die 12 including a plurality of low mass sensing structures 18 disposed within a thermally conductive substrate 16. The plurality of low mass sensing structures 18 of any advantageous size and shape include inter-structure spaces 20 of any advantageous shape to enhance the detection of gasses as they flows through the MEMS die 12.

While the present disclosure has been illustrated and described in detail in the drawings and foregoing description, the same is to be considered as illustrative and not restrictive in character, it being understood that only certain embodiments have been shown and described and that all changes and modifications that come within the spirit of the present disclosure are desired to be protected.

What is claimed is:

1. A microelectromechanical systems die comprising:
    a thermally conductive substrate including an outer surface;
    a plurality of sensing structures disposed within the thermally conductive substrate to form a plurality of inter-structure spaces therebetween, each of the plurality of sensing structures include a sensing structure proximal top surface, a sensing structure distal top surface, and a sensing structure width dimension;

a sensor material disposed on at least two surfaces of each of the plurality of sensing structures, the sensor material configured to detect a target gas;

a heating apparatus disposed on each of the plurality of sensing structures;

a sacrificial coating disposed on at least one of the plurality of sensing structures, wherein the sacrificial coating is disposed over the sensor material, wherein the sacrificial coating is composed of at least one material that is burned away by the heating apparatus;

wherein each heating apparatus disposed on each of the plurality of sensing structures is independently controlled by applying a separate current to each heating apparatus to independently control a temperature of the sensor material on each sensing structure.

2. The microelectromechanical systems die of claim 1, wherein at least two of the plurality of sensing structures include a different sensing structure width dimension.

3. The microelectromechanical systems die of claim 1, wherein the thermally conductive substrate is composed of silicon.

4. The microelectromechanical systems die of claim 1, further comprising a first electrode disposed on the sensor material at the sensing structure proximal top surface, and a second electrode disposed on the sensor material at the sensing structure distal top surface.

5. The microelectromechanical systems die of claim 1, further comprising at least one dielectric film disposed over the thermally conductive substrate.

6. The microelectromechanical systems die of claim 1, further comprising a plurality of passive heat exchangers, each operably coupled to a bond pad, wherein each bond pad is disposed on each of the at least one sensing structures.

7. The microelectromechanical systems die of claim 6, wherein the bond pad is operably coupled to at least one of the at least one electrode and the heating apparatus.

8. The microelectromechanical systems die of claim 5, further comprising at least one aperture disposed within the at least one dielectric film.

9. The microelectromechanical systems die of claim 8, further comprising a bond pad disposed within the aperture, wherein the bond pad is further coupled to a passive heat exchanger.

10. The microelectromechanical systems die of claim 1 further comprising at least one channel disposed within the thermally conductive substrate, wherein the at least one channel extends from the outer surface into at least one of the plurality of inter-structure spaces.

11. The microelectromechanical systems die of claim 10, further comprising a cavity disposed within the thermally conductive substrate, the cavity disposed beneath each of the plurality of sensing structures, and in flow communication with the at least one channel.

12. The microelectromechanical systems die of claim 1, wherein the sacrificial coating is composed of at least one of an organic material and a plastic material.

13. A gas detector package comprising:
a microelectromechanical systems die comprising:
a thermally conductive substrate;
a plurality of sensing structures disposed within the thermally conductive substrate, the plurality of sensing structures including a sensing structure proximal top surface, a sensing structure distal top surface, and a sensing structure width dimension;

a sensor material disposed on at least two surfaces of each of the plurality of sensing structures, the sensor material configured to detect a target gas;

a heating apparatus disposed on each of the plurality of sensing structures;

a sacrificial coating disposed on at least one of the plurality of sensing structures, wherein the sacrificial coating is disposed over the sensor material, wherein the sacrificial coating is composed of at least one material that is burned away by the heating apparatus;

wherein each heating apparatus disposed on each of the plurality of sensing structures is independently controlled by applying a separate current to each heating apparatus to independently control a temperature of the sensor material on each sensing structure.

14. The gas detector of claim 13, wherein at least two of the plurality of sensing structures include a different sensing structure width dimension.

15. The gas detector package of claim 13, wherein the thermally conductive substrate is composed of silicon.

16. The gas detector package of claim 13, wherein the microelectromechanical systems die further comprises a first electrode disposed on the sensor material at the sensing structure proximal top surface, and a second electrode disposed on the sensor material at the sensing structure distal top surface.

17. The gas detector package of claim 13, further comprising at least one dielectric film disposed over the thermally conductive substrate.

18. The gas detector package of claim 13, wherein the microelectromechanical systems die further comprises a plurality of passive heat exchangers, each operably coupled to a bond pad, wherein each bond pad is disposed on each of the at least one sensing structures.

19. The gas detector package of claim 18, wherein the bond pad is operably coupled to at least one of the at least one electrode and the heating apparatus.

20. The gas detector package of claim 17, wherein the microelectromechanical systems die further comprises at least one aperture disposed within the at least one dielectric film.

21. The gas detector package of claim 20, further comprising a bond pad disposed within the aperture, wherein the bond pad is further coupled to a passive heat exchanger.

22. The gas detector package of claim 13, wherein the microelectromechanical systems die further comprises at least one channel disposed within the thermally conductive substrate, wherein the at least one channel extends from the outer surface into at least one of the plurality of inter-structure spaces.

23. The gas detector package of claim 13, wherein the sacrificial coating is composed of at least one of an organic material and a plastic material.

* * * * *